(12) United States Patent
Liu et al.

(10) Patent No.: US 6,328,739 B1
(45) Date of Patent: Dec. 11, 2001

(54) ENHANCED SPINE FIXATION APPARATUS

(75) Inventors: Chien-Lin Liu, Taipei; Chi-Ming Shih, Hsin-Chu; Tze-Hong Wong, Hsinchu; Ben-Hwa Jang, Taipei; Wei-Tai Jao, Hsinchu; Chih-Ming Wu, Taipei; Chen-Dao Shaio, Hsinchu; Audy Choeo, Tao-Yuan, all of (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 09/436,268

(22) Filed: Nov. 8, 1999

(30) Foreign Application Priority Data

May 4, 1999 (TW) .................................................. 88207041

(51) Int. Cl.[7] .................................................. A61B 17/56
(52) U.S. Cl. .................................................. 606/61
(58) Field of Search .................................. 606/53, 60, 61, 606/62, 72, 73

(56) References Cited

U.S. PATENT DOCUMENTS

| 5,047,029 | * | 9/1991 | Aebi et al. ........................... 606/61 |
| 5,053,034 | * | 10/1991 | Olerud ................................ 606/61 |
| 5,129,900 | * | 7/1992 | Asher et al. ......................... 606/61 |
| 5,261,910 | | 11/1993 | Warden et al. . | |
| 5,403,314 | * | 4/1995 | Currier ............................... 606/61 |
| 5,474,551 | | 12/1995 | Finn et al. . | |
| 5,487,744 | * | 1/1996 | Howland ............................. 606/61 |
| 5,545,163 | | 8/1996 | Miller et al. . | |
| 5,735,850 | | 4/1998 | Baumgartner et al. . | |
| 5,735,852 | * | 4/1998 | Amrein et al. ....................... 606/61 |
| 5,741,255 | * | 4/1998 | Krag et al. .......................... 606/61 |
| 6,004,322 | * | 12/1999 | Bernstein ............................ 606/61 |
| 6,050,997 | * | 4/2000 | Mullane .............................. 606/61 |

* cited by examiner

Primary Examiner—Gene Mancene
Assistant Examiner—Eduardo C. Robert
(74) Attorney, Agent, or Firm—Ladas & Parry

(57) ABSTRACT

An enhanced spine fixation apparatus for fixing a number of vertebrae of a spine column is disclosed. The spine fixation apparatus comprises a plurality of pedicel screws, a plurality of coupling blocks, a plurality of first securing elements, a plurality of second securing elements, a connecting rod, and a plurality of third securing elements. Each coupling block is secured on a pedicel screw by the first securing element while the connecting rod is secured on the coupling block by the second securing element. Each first securing element is fixed by the third securing element. By virtue of the provisions of a first and a second spherical convex surfaces as well as a first and a second recesses respectively on the surfaces of the pedicel screw and the first securing element as well as the surfaces of the coupling block which are being abutted, an adjustment concerning a vertical tilt angle and a horizontal rotating angle of the coupling block relative to the pedicel screw is available. By way of the third securing element, the first securing element is prevented from loosening.

4 Claims, 2 Drawing Sheets

ENHANCED SPINE FIXATION APPARATUS

BACKGROUND OF THE INVENTION

1. Field of the Invention

The invention relates to a spine fixation apparatus, and more particularly to an enhanced spine fixation apparatus having a compact mechanism adjustable in three dimensions and an enhanced combination.

2. Description of the Prior Art

A spine fixation apparatus is an internal fixation system for fixing at least two vertebrae of the spine for the benefit of promoting recovery of a damaged spine. The spine fixation apparatus is usually made of stainless or special material and is widely used in line with the progress and development of surgical procedures. However, there are still some drawbacks existing in the known various spine fixation apparatuses, such as inconvenience to adjust in an arbitrary direction, damage to soft tissue, and inconvenience to operate. Such drawbacks occur in the light of the fact that the components in a spine fixation apparatus should be properly adjusted so as to conform to the anatomical structure of a patient and to eliminate stress subjected therein. In addition, even if a spine fixation apparatus adjustable in many axes has been developed in the prior art, it includes lots of components and requires a complicated assembly procedure, which in turn places a heavy stress one the surgeon and surgical staff. Also, a long duration for surgery may be required and thus patient morbidity resulting from blood loss and stress of anesthesia may increase.

In U.S. Pat. No. 5,474,551, a spinal fixation device which allows for adjustment in four axes with respect to an attachment of a longitudinal rod to vertebrae of a spinal column is disclosed. However, such a device consists of a multitudes of complicated components and tends to loosen. Moreover, a helical thread is provided on the exterior surface of a distal end of a pedicel screw for coupling other components, such as nut, and thus damage to soft tissue is possible due to exposure of threads after assembly. In U.S. Pat. No. 5,545,163, a spine fixation system comprising an elongated fixation plate is disclosed, in which the position of the plate to be fixed can be selected according to pitches of the pedicel screws. However, the range to be selected is segmental and the orientation of the spine fixation system is not able to be adjusted sufficiently. Further, a helical thread is also provided on the exterior surface of the distal end of a pedicel screw and thus soft tissue damage after assembly is also possible. In U.S. Pat. No. 5,261,910, a pedicel screw provided with a threaded hole at its distal end to couple with a screw is disclosed. However, such a construction fails to allow for an adjustment corresponding to the distance of two pedicel screws and the oblique angles of pedicel screws implanted into the vertebrae. In U.S. Pat. No. 5,735,850, a fastening system for pedicel screws each having a threaded hole at its distal end is disclosed, in which the angle of a connecting member relative to each pedicel screw can be adjusted by the provision of a counter-part capable of sliding against the surface of the connecting member. However, the fixed points of said connecting member cannot be freely selected in so far as to conform to the pitch of two pedicel screws.

SUMMARY OF THE INVENTION

It is therefore an object of the present invention to provide an enhanced spine fixation apparatus capable of inclusively overcoming the above drawbacks, which is conveniently installed, easily adjusted for compensating implanting deviation of pedicel screws, and able to avoid damage to soft tissue.

Another object of the present invention is to provide a spine fixation apparatus having a more stable coupling between components thereof.

In order to achieve the above objects, an enhanced spine fixation apparatus according to this invention comprising:

a connecting rod;

a plurality of coupling blocks each having a lower side surface and an upper side surface;

a plurality of pedicel screws each being anchorable in a vertebra;

a plurality of first securing elements each for securing the coupling blocks on the pedicel screws respectively;

a plurality of second securing elements each for securing the connecting rod on each of the coupling blocks; and a plurality of third securing elements each having an engaging end surface for engaging with each of the first securing elements;

wherein, each of the pedicel screws includes a first head portion having a first spherical convex surface at a top end surface thereof, and a first engaging hole longitudinally extending substantially along a longitudinal axis of each of the screws and opening to the first convex surface;

each of the first securing elements includes:
a shank portion to be detachably secured in the first engaging hole of the pedicel screw; and
a second head portion having a second spherical convex surface disposed at a top of the shank portion; and each of the coupling blocks includes:
a first socket for the shank portion of the first securing element passing therethrough, in which the first socket includes a first recess opening to the lower side surface and defined by a first concave surface for accommodating and matching with at least a portion of the first head portion, a second recess opening toward the upper side surface and defined by a second concave surface for accommodating and matching with the second head portion with a spacing left between portions of the second spherical convex surface and the second concave surface, and an aperture extending between and opening to the bottoms of the first and the second recesses and having a diameter larger than that of the shank portion and smaller than a largest diameter at either of the first and the second head portions;
a second socket substantially axially perpendicular to the first socket, for the connecting rod accommodated therein;
a second engaging hole substantially axially perpendicular to the second socket for securing the connecting rod in cooperation with the second securing element; and
a third engaging hole communicating with the second recess and opening to the upper side surface of the coupling block for engaging with the third securing elements so that the engaging end surface of the third securing element forces the first securing element against the coupling block.

According to the above structure, users could install in sequence each component of the spine fixation apparatus on the spine with a driving force in a direction coming down from the upside over a spine. Moreover, the vertical tilt angle of each coupling block relative to each pedicel screw can be moderately adjusted and the horizontal rotating angle thereof can be arbitrarily adjusted, and thus an adjustment of each coupling block relative to each pedicel screw in three dimensions is available. Accordingly, even if the implanting angle of the pedicel screw has little deviation, it could be easily compensated by the adjustment of the inclination and rotation of the coupling block relative to the pedicel screw. Furthermore, since an engaging hole is used by the pedicel screw to receive the distal end of the first securing element, soft tissue probably would not be damaged. And, by means of the provision of the third securing elements and the third engaging holes, the first securing elements could be more stably retained in the pedicel screws and thereby firmly secure the coupling blocks. Therefore, it is possible to obtain an enhanced spine fixation apparatus which is simply constructed, conveniently operated, easily adjusted, and firmly assembled, as well as being non damaging to soft tissue.

These and the other objects, characteristics and effects of this invention will become clearer based upon the following detailed description with regard to this invention.

DETAILED DESCRIPTION OF THE INVENTION

Figure 1:
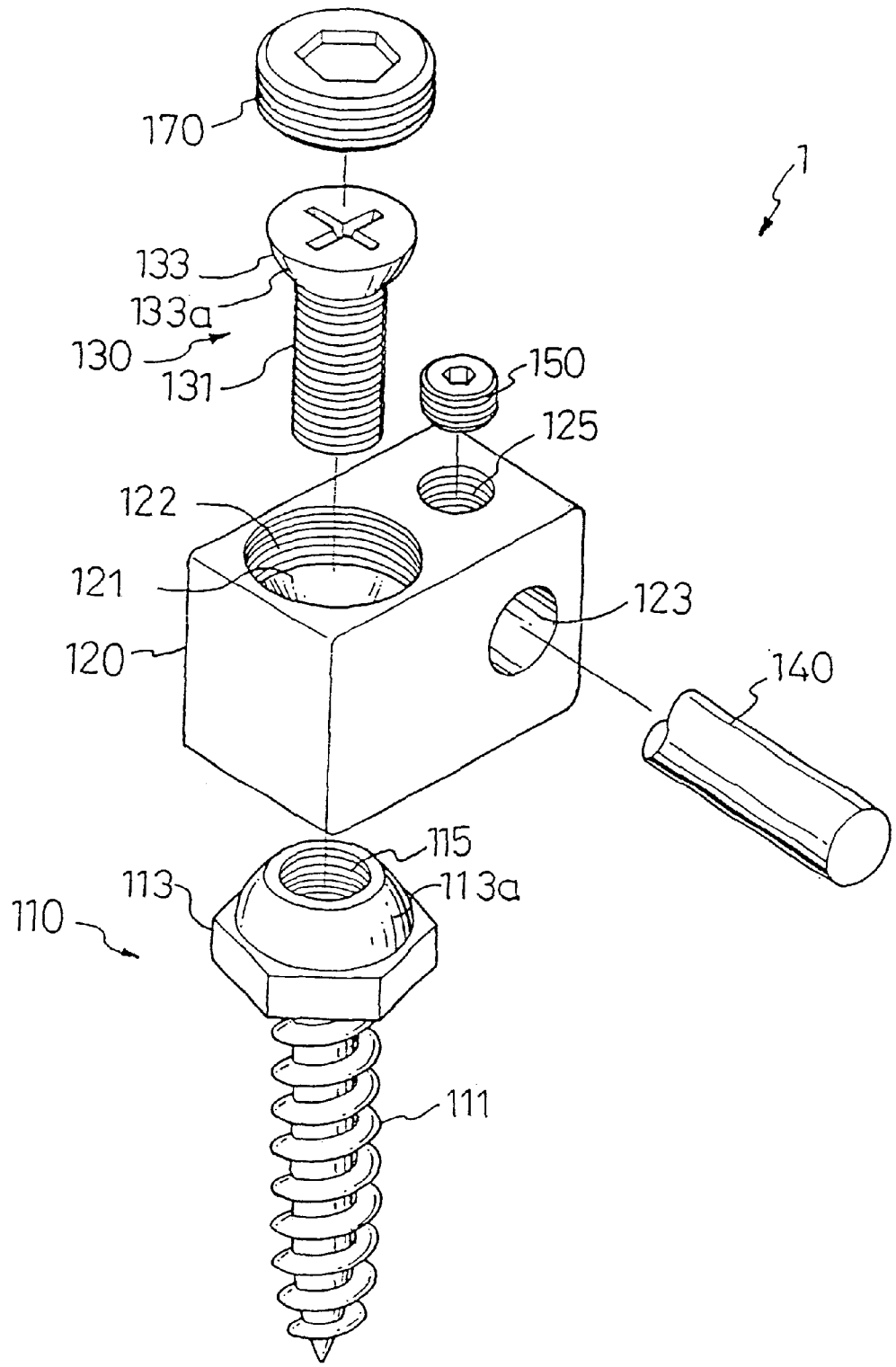
FIG. 1 is an exploded perspective view of a spine fixation apparatus according to a preferred embodiment of this invention.

As shown in FIG. 1, an enhanced spine fixation apparatus 1 according to a preferred embodiment of this invention generally comprises: a plurality of pedicel screws 110, a plurality of coupling blocks 120, a plurality of inner bolts 130 functioning as first securing elements for respectively securing the coupling blocks 120 on the pedicel screws 110, a connecting rod 140, a plurality of set bolts 150 functioning as second securing elements for respectively securing the connecting rod 140 on the coupling blocks 120, and a plurality of outer plugs 170 for engaging with and fixing the inner bolts 130.

Each pedicel screw 110 comprises a body portion 111 to be implanted into a vertebra of a spine (not shown in the drawings), a first head portion 113 having a first spherical convex surface 113a at the top end surface thereof, and an threaded cave 115 opening to the first spherical convex surface 113a and longitudinally extending substantially along the longitudinal axis of the pedicel screw 110, which functions as a first engaging hole. The body portion 111 is provided with a helical thread on its exterior surface so that is can be implanted into the vertebra by screws.

Each inner bolt 130 comprises a shank portion 131 provided with threads for detachably engaging with the threaded cave 115, and a flat second head portion 133 having a second spherical convex surface 133a which extends from an interface with the shank portion 131 toward the top end surface of the second head portion 133. Moreover, there is a phillips provided in the top end surface for being driven.

Each outer plug 170 is provided with an upper driven end surface having a hexagonal recess to be driven, a lower engaging end surface for depressing the second head portion of the inner bolt 130, and a threaded cylindrical surface between the upper and lower end surfaces.

Each coupling block 120 comprises a first socket 121 for the pass of the shank portion 131 of the inner bolt 130, a second socket 123 for the pass of the connecting rod 140, a threaded hole 125 functioning as a second engaging hole for engaging with the set bolt 150, and a threaded hole 122 functioning as a third engaging hole for engaging with the outer plug 170.

Figure 2:
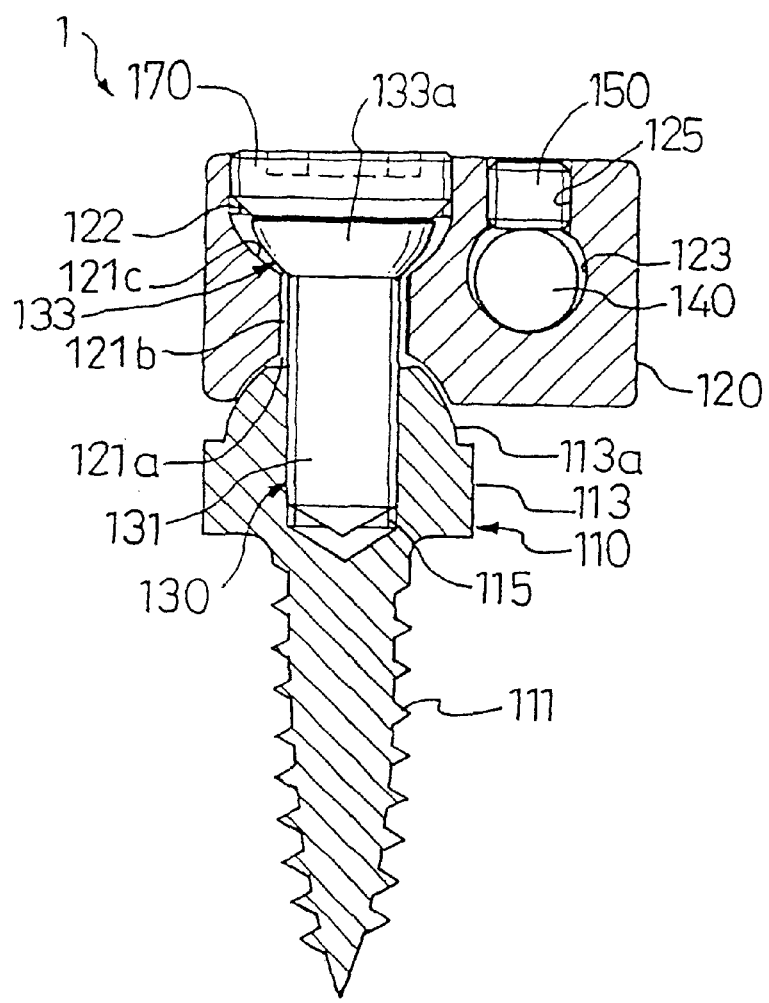
FIG. 2 is a partial sectional view of the spine fixation apparatus shown in FIG. 1 after being assembled.

As shown in FIG. 2, the first socket 121 consists of a first recess 121a opening to a lower side surface of the coupling block 120 and defined by a first concave surface, a second recess 121c opening toward an upper side surface of the coupling block 120 and defined by a second concave surface, and an aperture 121b extending between and opening to the bottoms of the first and the second recesses 121a, 121c.

The aperture 121b has a diameter larger than the diameter of the shank portion 131 of the inner bolt 130 but smaller than the largest diameter of the first and the second head portions 113, 133 so as to allow merely a pass-way for the shank portion 131 of the inner bolt 130. The first concave surface has a curvature substantially identical to the first convex surface 113a and can accommodate and match with at least a portion of the first convex surface 113a so as to be supported thereby at an angle. The second recess 121c has an upper opening of which the diameter is larger than the largest diameter of the second head portion 133. The second concave surface has a curvature smaller than the second convex surface 133a. Thus, at least a portion of the second head portion 133 of the inner bolt 130 could fall into the second recess 121c and matches with a portion of the second concave surface, in which there is a spacing left between portions of the second spherical convex surface 133a and the second concave surface. In other words, the axis of the aperture 121b could be tilted relative to that of the inner bolt 130 at a proper angle.

The threaded hole 122 upward opens to the upper side surface of the coupling block 120, downward communicates with the second recess 121c, and is defined by a threaded wall, functioning as an engaging wall, for engaging with the outer plug 170 so that the engaging end surface of the outer plug 170 can prevent the inner bolt 130 from loosening.

The second socket 123 is in the form of a straight hole spaced from the first socket 121 and having an axis substantially perpendicular to the first socket 121. The threaded hole 125 upward opens to the upper side surface of the coupling block 120 and downward communicates with the second shock 123. By means of the cooperation of the threaded hole 125 and the set bolt 150, a distal end of the set bolt 150 can be depressed on the connecting rod 140 and thereby secure the connecting rod 140 in the coupling block 120.

In the following, a procedure concerning the assembly of the spine fixation apparatus 1 having the above structure will be described with reference to FIG. 2.

As shown in FIG. 2, each pedicel screw 10 (only one pedicel screw is shown in the drawings for illustrative purposes) is fixed to each vertebra (not shown in the drawings) with its body portion 111. Each coupling block 120 is then put onto the first head portion 113 with an alignment of the first socket 121 and the threaded cave 115. Then the inner bolt 130 is inserted and slightly screwed into the threaded cave 115 through the first socket 121. Continuously, the connecting rod 140 is pre-curved and placed into the second socket 123, in which the orientation of the coupling block 120 relative to the pedicel screw 110 is so adjusted that the connecting rod 140 would be smoothly coupled to the coupling block 120 while the first spherical convex surface 113a and the first recess 121a are matched. Following, the set bolt 150 is screwed into the threaded hole 125 of the coupling block 120 and then the inner bolt 130 can be further firmly screwed into the threaded cave 115. In the above procedure, since the diameter of the aperture 121b is larger than that of the shank portion 131 of the inner bolt 130, and since there is a spacing left between portions of the second spherical convex surface 133a and the second recess 121c, the vertical tilt angle of the coupling block 120 relative to the pedicel screw 110 could be adjusted to comply with the connecting rod 140, at about ten degrees, and the coupling block 120 could be firmly secured on the pedicel screw 110 by the inner bolt 130. Lastly, the outer plug 170 is screwed into the threaded hole 122 until the lower engaging end surface thereof engages with the inner bolt 130. Thus, the assembly of the spine fixation apparatus 1 is accomplished.

Figure 3:
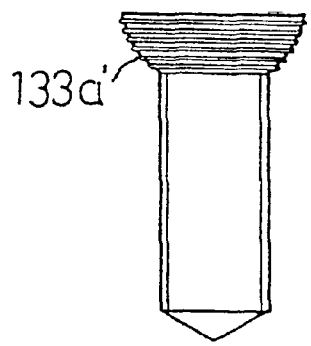
FIG. 3 is a front view showing an alternative of the second spherical convex surface shown in the embodiment of this invention.

FIG. 3 illustrates an alternative of the second head portion 133 of the inner bolt 130 shown in the preferred embodiment. As shown in FIG. 3, there are a plurality of annular crinkles (not indicated) formed on the second spherical convex surface 133a'. By means of these crinkles, the second spherical convex surface 133a' could more stably engage with the second concave surface 121c.

In view of the above, the spine fixation apparatus according to this invention does have a compact structure and provides an adjustability of the coupling block relative to the pedicel screw in three dimensions. Moreover, the mechanism for coupling the connecting rod and pedicel screws can avoid soft tissue damage. Also, each component of the spine fixation apparatus can be assembled with a driving force in a direction from the upside and thus it is convenient for assembly. Furthermore, by virtue of the outer plug 170, the assembly of the spine fixation apparatus is more stable and rigid.

While this invention has been described by illustrations, various equalivent modifications and variants could be contemplated without departing from the scope and spirit of the present invention. For example, the first and the second concave surfaces could be any possible shapes, such as a column surface in place of the illustrated spherical surface. Therefore, the present invention is intended to be limited only as indicated in the following claims.

What is claimed is:

1. A spine fixation apparatus, comprising:
    a connecting rod;
    a plurality of coupling blocks each having a lower side surface and an upper side surface;
    a plurality of pedicel screws each being anchorable in a vertebra;
    a plurality of first securing elements each for securing the coupling blocks on the pedicel screws respectively;
    a plurality of second securing elements each for securing the connecting rod on each of the coupling blocks; and
    a plurality of third securing elements each having an engaging end surface for engaging with each of the first securing elements;
    wherein, each of the pedicel screws includes a first head portion having a first spherical convex surface at a top end surface thereof, and a first engaging hole longitudinally extending substantially along a longitudinal axis of each of the screws and opening to the first convex surface;
    each of the first securing elements includes:
        a shank portion to be detachably secured in the first engaging hole of the pedicel screw; and
        a second head portion having a second spherical convex surface disposed at a top of the shank portion; and
    each of the coupling blocks includes:
        a first socket for the shank portion of the first securing element passing therethrough, in which the first socket includes a first recess opening to the lower side surface and defined by a first concave surface for accommodating and matching with at least a portion of the first head portion, a second recess opening toward the upper side surface and defined by a second concave surface for accommodating and matching with the second head portion with a spacing left between portions of the second spherical convex surface and the second concave surface, and an aperture extending between and opening to the bottoms of the first and the second recesses and having a diameter larger than that of the shank portion and smaller than a largest diameter at either of the first and the second head portions;
        a second socket substantially axially perpendicular to the first socket, for the connecting rod accommodated therein;
        a second engaging hole substantially axially perpendicular to the second socket for securing the connecting rod in cooperation with the second securing element; and
        a third engaging hole communicating with the second recess and opening to the upper side surface of the coupling block for engaging with the third securing element so that the engaging end surface of the third securing element forces the first securing element against the coupling block.

2. The spine fixation apparatus of claim 1, wherein the first concave surface is of a spherical shape and has a curvature identical to the first convex surface.

3. The spine fixation apparatus of claim 2, wherein the second convex surface is provided with a plurality of annular crinkles to avoid a glide between the second convex surface and the second concave surface.

4. The spine fixation apparatus of claim 1, wherein the second concave surface is of a spherical shape and has a curvature smaller than the second convex surface.

* * * * *